US010258512B2

United States Patent
Vartiainen et al.

(10) Patent No.: US 10,258,512 B2
(45) Date of Patent: Apr. 16, 2019

(54) ELECTRONICS ENCLOSURE AND RECEPTACLE

(71) Applicant: SCA Hygiene Products AB, Göteborg (SE)

(72) Inventors: Kent Vartiainen, Lerum (SE); Sofia Hermansson, Västra Frölunda (SE)

(73) Assignee: ESSITY HYGIENE AND HEALTH AKTIEBOLAG, Göteborg (SE)

(*) Notice: Subject to any disclaimer, the term of this patent is extended or adjusted under 35 U.S.C. 154(b) by 659 days.

(21) Appl. No.: 14/777,536

(22) PCT Filed: Mar. 19, 2013

(86) PCT No.: PCT/EP2013/055686
§ 371 (c)(1),
(2) Date: Sep. 16, 2015

(87) PCT Pub. No.: WO2014/146693
PCT Pub. Date: Sep. 25, 2014

(65) Prior Publication Data
US 2016/0067113 A1    Mar. 10, 2016

(51) Int. Cl.
*A61F 13/42* (2006.01)
*A61F 13/84* (2006.01)
*A61F 13/15* (2006.01)

(52) U.S. Cl.
CPC .............. *A61F 13/42* (2013.01); *A61F 13/84* (2013.01); *A61F 2013/15146* (2013.01); *A61F 2013/424* (2013.01); *A61F 2013/8479* (2013.01)

(58) Field of Classification Search
CPC .... A61F 13/42; A61F 13/84; A61F 2013/424; A61F 2013/8479
See application file for complete search history.

(56) References Cited

U.S. PATENT DOCUMENTS 5,790,036 A * 8/1998 Fisher .................. A61F 13/42
                                                   128/886
7,250,547 B1   7/2007 Hofmeister et al.
(Continued)

FOREIGN PATENT DOCUMENTS

CN    101784247 A    7/2010
JP    H07239990 A    9/1995
(Continued)

OTHER PUBLICATIONS

First Chinese Office Action dated Jan. 10, 2018 issued in corresponding Chinese patent application No. 201380074892.3 (9 pages) and its English-language translation thereof (10 pages).
(Continued)

*Primary Examiner* — Catharine L Anderson
(74) *Attorney, Agent, or Firm* — Drinker Biddle & Reath LLP

(57) ABSTRACT

An electronics enclosure has terminal conductors for contacting corresponding conductors in a receptacle when engaged with the receptacle. The electronics enclosure has a housing having first, second, third, fourth, fifth and sixth surface portions arranged to define the exterior of the housing. The receptacle engages and retains the corresponding electronics enclosure, the receptacle having terminal conductors for contacting corresponding conductors in the enclosure when engaged with the enclosure. The receptacle has a base surface along which the enclosure can translate in an engagement direction to engage the enclosure with the receptacle. An absorbent article management system includes: a diaper having the receptacle at which sensor elements of the diaper terminate; a logger unit having logger electronics enclosed in the enclosure and adapted to cooperate with the receptacle to connect the logger electronics to the sensor elements; and data processing equipment for processing data acquired from the sensor elements by the logger and for taking action based on the same.

23 Claims, 18 Drawing Sheets

(56) References Cited

U.S. PATENT DOCUMENTS

| | | |
|---|---|---|
| 7,977,529 B2 | 7/2011 | Bergman et al. |
| 2003/0031591 A1 | 2/2003 | Whitson et al. |
| 2005/0156744 A1 | 7/2005 | Pires |
| 2005/0195085 A1* | 9/2005 | Cretu-Petra .......... A61B 5/6808 340/573.5 |
| 2005/0225449 A1 | 10/2005 | Blakeway |
| 2007/0204691 A1 | 9/2007 | Bogner et al. |
| 2008/0243099 A1 | 10/2008 | Tippey et al. |
| 2009/0062756 A1 | 3/2009 | Long et al. |
| 2011/0083757 A1 | 4/2011 | Shore et al. |
| 2011/0263952 A1 | 10/2011 | Bergman et al. |
| 2011/0295619 A1 | 12/2011 | Tough |

FOREIGN PATENT DOCUMENTS

| | | |
|---|---|---|
| JP | 2004-529730 A | 9/2004 |
| JP | 2010-537694 A | 12/2010 |
| WO | WO-94/02918 A1 | 2/1994 |
| WO | WO-96/14813 A1 | 5/1996 |
| WO | WO-00/00144 A2 | 1/2000 |
| WO | WO-02/101679 A1 | 12/2002 |
| WO | WO-2004/100763 A2 | 11/2004 |
| WO | WO-2006/47815 A1 | 5/2006 |
| WO | WO-2009/069115 A1 | 6/2009 |
| WO | WO-2011/054045 A1 | 5/2011 |
| WO | WO-2011/126497 A1 | 10/2011 |
| WO | WO-2011/156862 A1 | 12/2011 |

OTHER PUBLICATIONS

Canadian Office Action dated Jul. 10, 2017 issued in corresponding Canadian patent application No. 2,906,966 (4 pages).
European Office Action dated Apr. 5, 2017 issued in corresponding European patent application No. 13 711 636.4 (5 pages).
English-language translation of a Russian Office Action dated Apr. 4, 2017 issued in corresponding Russian patent application No. 2015144588 (5 pages).
Second Chinese Office Action dated Aug. 9, 2018 issued in corresponding Chinese patent application No. 201380074892.3 (10 pages) and its English-language translation thereof (8 pages).

* cited by examiner

ELECTRONICS ENCLOSURE AND RECEPTACLE

CROSS-REFERENCE OF RELATED APPLICATIONS

This application is a § 371 National Stage Application of PCT International Application No. PCT/EP2013/055686 filed Mar. 19, 2013, which is incorporated herein in its entirety.

TECHNICAL FIELD

The present disclosure relates to an electronics enclosure and a corresponding receptacle, and in particular an electronics enclosure and corresponding receptacle which may be provided in engageable or engaged cooperation for providing an absorbent article, such as such a diaper, a sanitary towel, an incontinence garment, a medical dressings and the like, with sensing and/or datalogging capabilities. Especially, the electronics enclosure is suitable to be provided, or may be provided, with sensing and/or datalogging electronics for attachment and connection to an absorbent article having sensors, while the receptacle is suitable to be provided or may be provided attached to an absorbent article having sensors such that an enclosure includes sensing and/or datalogging electronics may be engaged with the receptacle to connect to the sensors.

TECHNICAL BACKGROUND

Absorbent articles, such as diapers, sanitary towels, incontinence garments, medical dressings and the like, have widespread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g. to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Since absorbent articles are available in a variety of absorbent capacities, the user or carer must also determine, from those products which are available, which capacity of article to select. For example, in some circumstances it may be preferable to select an article of a lower capacity which is changed more frequently in contrast to an article of relatively larger capacity which is changed less frequently. Factors influencing this choice will be the nature of the absorption required, i.e. whether intermittent large quantities or a continuous smaller rate, as well as the total volume expected to be absorbed during a given period of time.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established and appropriate absorbent articles provided.

Systems which are able to alert the user or carer to saturation or impending saturation of the absorbent article are therefore of benefit. Furthermore, systems which are able to monitor the usage pattern of a particular absorbent article, and of a series of absorbent articles associated with a particular individual, over a period of time, are of particular benefit.

Such systems may take the form of an absorbent article having embedded sensors which connect to a logger unit to monitor and record the sensor data over time. The sensors can, for example, be moisture sensors. When the absorbent capacity of the absorbent article is approached or exceeded, the user or the carer can be notified, on the basis of the recorded sensor data, that the absorbent article requires replacement.

Additionally, data obtained from a particular user over time can be used to monitor both the health of the user and the appropriateness of the absorbent article for that user over an extended period and can be used to provide better information for the care of the user. For example, an event, such as an incontinence event, leading to saturation of the article can be predicted and action, such as toileting action, taken before the event occurs.

One exemplary system is shown in FIG. 1, in which an absorbent article 400, exemplified here as a diaper and having a waistband 410 and an absorbent area 420, is provided with a logger unit 300 attached to the waistband 410 and having sense wires 430 extending from the logger unit 300 running through the absorbent area. The sense wires 430 may be used to detect moisture, for example by detecting changes in the conductivity between the wires. The sense wires may be only partly exposed to the absorbent area, for example by providing insulation, to localise the region of sensing. The particular wiring pattern depicted is wholly exemplary, and will be selected according to the sensing requirements.

The logger unit 300, comprising data-logging electronics such as a power source, processor, memory, instruction store, data store, communications bus, and data link interface, which cooperate to store, process, and/or forward the data derived from sense wires, is connected by data link 500 to a data receiver 600. In the example of FIG. 1, data link 500 is a wireless data link, and data receiver 600 is a wireless data receiver. However, it is also possible that a docking functionality can be provided between the logger 300 and a docking station functioning as data receiver 600 to transfer data recorded in the logger 300 when the logger 300 is placed into the docking station. In a further alternative, data link 500 can be provided over the cellular telephone network, in which case data receiver 600 may be implemented as a cellular base station.

The data received at data receiver 600 is then transmitted by a further data link 700 to data processing equipment 800, exemplified as computer terminal 810 and output device 820 mutually connected by data link 830. Here, the computer terminal 810, which is an example of a general purpose data processing device, conducts processing on the sensor data received from the logger unit 300 via data links 500 and 700 and data receiver 600 and takes action based on the same, for example by outputting alerts, predictions, or statistics via output device 820. Here, the output device is shown as a line printer, but could, for example, be another form of hard copy printer, a visual display unit, a visual alarm panel, or an audio output device, without limitation.

Such a system may provide a powerful tool for the management of users of absorbent articles.

However, absorbent articles are conventionally disposable absorbent articles for reasons of hygiene and convenience. Although reusable absorbent articles are known, they are rarely used, especially in institutional and clinical settings, for reasons of economy and hygiene, amongst others.

Therefore, in the arrangement of FIG. 1, since the logger unit 300 is connected to sensor wires 430, which extend through the article 400, when the absorbent article 400 is to be discarded after a use, the logger unit 300 must be discarded also. However, the logger unit 300 is generally far more costly than the article 400 to manufacture. Thus, the system of FIG. 1 may be very expensive to operate, especially for an extended period of time. Further, the disposal of repeated disposal of electronic waste becomes environmentally unsound. Furthermore, discarding the logger 300 with the article 400 provides a data management challenge for the user, the carer or the institution, in assuring that when a new diaper with logger is provided to a user to replace a discarded diaper with logger, the logger is correctly initialised and data linking the logger to the user are correctly recorded.

The present disclosure provides a solution to this problem, as described more fully below.

SUMMARY

According to a first aspect, there is provided an electronics enclosure for engagement with a cooperating receptacle, the electronics enclosure having terminal conductors for contacting corresponding conductors in the receptacle when engaged with the receptacle, the electronics enclosure having a housing, the housing having first, second, third, fourth, fifth and sixth surface portions arranged to define the exterior of the housing, the first and second surface portions being respectively front and rear surface portions in an engagement direction of the enclosure with the receptacle, the third and fourth surface portions each connecting the first and second surface portions, the fifth and sixth surface portions each connecting the first and second surface portions and each connecting the third and fourth surface portions and being spaced apart in a direction other than the engagement direction, and the housing having no more than one plane of symmetry which includes the engagement direction.

According to a second aspect, there is provided an electronics enclosure for engagement with a corresponding receptacle, the electronics enclosure having terminal conductors for contacting corresponding conductors in the receptacle when engaged with the receptacle, the electronics enclosure having a housing, the housing having first, second, third, fourth, fifth and sixth surface portions arranged to define the exterior of the housing, the first and second surface portions being respectively front and rear surface portions in an engagement direction of the enclosure with the receptacle, the third and fourth surface portions each connecting the first and second surface portions, the fifth and sixth surface portions each connecting the first and second surface portions and each connecting the third and fourth surface portions and being spaced apart in a direction other than the engagement direction, and the third and fourth surface portions each being provided with a locking depression or projection for engaging a corresponding portion of the receptacle to retain the enclosure within the receptacle.

According to a third aspect, there is provided an electronics enclosure for engagement with a corresponding receptacle, the electronics enclosure having terminal conductors for contacting corresponding conductors in the receptacle when engaged with the receptacle, the electronics enclosure having a housing, the housing having first, second, third, fourth, fifth and sixth surface portions arranged to define the exterior of the housing, the first and second surface portions being respectively front and rear surface portions in an engagement direction of the enclosure with the receptacle, the third and fourth surface portions each connecting the first and second surface portions, the fifth and sixth surface portions each connecting the first and second surface portions and each connecting the third and fourth surface portions and being spaced apart in a direction other than the engagement direction, the third and fourth surface portions each including a locking depression or projection for engaging a corresponding element of the receptacle to retain the enclosure within the receptacle, and the housing having a depression on an edge joining the rear and lower surface portions and extending at least partly across those surface portions from the edge.

In some embodiments, the third and fourth surface portions each include one of a locking protrusion and depression for engaging a corresponding element of the receptacle to retain the enclosure within the receptacle.

In some embodiments, the housing has a depression on an edge joining the rear and lower surface portions and extending at least partly across those surface portions from the edge.

In some embodiments, the housing has no more than one plane of symmetry which includes the engagement direction.

In some embodiments, the third and fourth surface portions are relatively inclined to approach each other in the engagement direction from the second to the first surface portion.

In some embodiments, the third and fourth surface portions are each provided with a groove or rail for engaging a retaining portion of the receptacle and extending at least partly along each surface portion from the first surface portion to the second surface portion.

In some embodiments, the locking depression or projection is located at the groove or rail.

In some embodiments, each groove or rail is provided parallel to an edge joining the respective third or fourth surface portion to the fifth surface portion.

In some embodiments, each groove or rail is provided relatively closer to an edge joining the third or fourth surface portion, respectively, to one of the fifth and sixth surface portions than to an edge joining the third or fourth surface portion, respectively, to the other of the fifth and sixth surface portions.

In some embodiments, the fifth and sixth surface portions have different radii of curvature in a plane perpendicular to the engagement direction.

In some embodiments, the fifth surface portion is configured to support the terminal conductors and the sixth surface portion has a radius of curvature smaller than that of the fifth surface portion in a plane perpendicular to the engagement direction.

In some embodiments, wherein at least one pair of surface portions, selected from: i) the pair of the third and fourth surface portions; and ii) the pair of the fifth and sixth surface portions, are provided with texture that differs one from the other.

In some embodiments, the fifth surface portion is substantially planar.

In some embodiments, the fifth and sixth surface portions have perimeters which are isosceles trapezoidal.

In some embodiments, the second and third surface portions have perimeters which are rectangular.

In some embodiments, the enclosure has rounded corners where the sixth surface portion meets at least any two of the first to fourth surface portions.

In some embodiments, at least one of the first and second surface portions are curved outwardly in a direction respectively along or opposed to the engagement direction.

In some embodiments, the sixth surface portion is curved outwardly in a direction perpendicular to the engagement direction.

In some embodiments, the enclosure contains logging electronics connected to terminals provided on an exterior of the enclosure and configured to receive and process sensor signals from an absorbent article via the terminals.

According to a fourth aspect, there is provided a receptacle for engaging and retaining a corresponding electronics enclosure, the receptacle having terminal conductors for contacting corresponding conductors in the enclosure when engaged with the enclosure, the receptacle having a base surface along which the enclosure can translate in an engagement direction to engage the enclosure with the receptacle, and the receptacle being configured such that the receptacle becomes narrower in a direction across the engagement direction with increasing distance into the receptacle along the engagement direction.

According to a fifth aspect, there is provided a receptacle for engaging and retaining a corresponding electronics enclosure, the receptacle having terminal conductors for contacting corresponding conductors in the enclosure when engaged with the enclosure, the receptacle having a base surface along which the enclosure can translate in an engagement direction to engage the enclosure with the receptacle, and the receptacle having at least two locking elements selected from i) a locking protrusion and ii) a locking depression for engaging corresponding elements of the enclosure and positioned at opposite edges of the base surface across the engagement direction.

According to a sixth aspect, there is provided a receptacle for engaging and retaining a corresponding electronics enclosure, the receptacle having terminal conductors for contacting corresponding conductors in the enclosure when engaged with the enclosure, and the receptacle having a base surface along which the enclosure can translate in an engagement direction to engage the enclosure with the receptacle, the receptacle having a grip protrusion extending rearwards relative to the engagement direction from a rear edge of the base surface.

In some embodiments, the receptacle has at least two locking elements selected from i) a locking protrusion and ii) a locking depression for engaging corresponding elements of the enclosure and positioned at opposite edges of the base surface across the engagement direction.

In some embodiments, the receptacle further comprises a grip protrusion extending rearwards relative to the engagement direction from a rear edge of the base surface.

In some embodiments, a rear surface of the grip protrusion has a concave rearmost end surface.

In some embodiments, the receptacle is configured such that the receptacle becomes narrower in a direction across the engagement direction with increasing distance into the receptacle along the engagement direction.

In some embodiments, the receptacle has a front stop portion extending from the forward edge of the base surface in the engagement direction and arranged to inhibit further movement of the enclosure in the engagement direction once the enclosure is engaged with the receptacle.

In some embodiments, the stop portion is provided as a barrier extending along the forward edge of the base portion.

In some embodiments, the barrier has a lowered portion intermediate along the forward edge of the base portion, the height of which from the base portion is less than that of portions of the barrier adjoining the lowered portion.

In some embodiments, the barrier is a wall.

In some embodiments, the receptacle has at least two guide elements selected from i) a guide rail and ii) a guide groove for engaging corresponding portions of the enclosure each positioned at opposite edges of the base surface across the engagement direction, and each running parallel to said edges of the base surface.

In some embodiments, the guide elements are formed at side wall portions extending from said opposite edge portions of the base surface.

In some embodiments, the locking elements are each provided on a flexible lock support extending from said opposite edge portions of the base surface.

In some embodiments, the locking elements are provided adjacent to ends of the guide elements at substantially the same height above the base surface as the ends of the guide elements.

In some embodiments, as at least one of the guide elements, a guide rail is provided relatively forward in the engagement direction to a respective locking protrusion at the same edge portion as the guide rail.

In some embodiments, as at least one of the guide elements, a guide groove is provided relatively rearward in the engagement direction to a respective locking depression at the same edge portion as the guide groove.

In some embodiments, the base surface has a substantially isosceles trapezoidal shape.

In some embodiments, the receptacle is provided in combination with an absorbent article having sensor elements, the sensor elements being terminated at the receptacle.

According to a seventh aspect, there is provided a combination of an enclosure being an embodiment of any one of the first to third aspects and a cooperating receptacle being an embodiment of any one of the fourth to sixth aspects.

According to an eighth aspect, there is provided an absorbent article management system comprising: a diaper having a receptacle being an embodiment of any one of the fourth to sixth aspects at which sensor elements of the diaper terminate; a logger unit having logger electronics enclosed in an enclosure being an embodiment of any one of the first to third aspects and adapted to cooperate with the receptacle to connect the logger electronics to the sensor elements; and data processing equipment for processing data acquired from the sensor elements by the logger and for taking action based on the same.

BRIEF DESCRIPTION OF THE DRAWINGS

To better understand the present invention, and to show how the same may be put into effect, reference will be made, by way of example only, to the accompanying Drawings showing embodiments of the present invention, in which.

DETAILED DESCRIPTION OF PARTICULAR EMBODIMENTS

Embodiments of the present invention will now be described with reference to the Figures.

Figure 1:
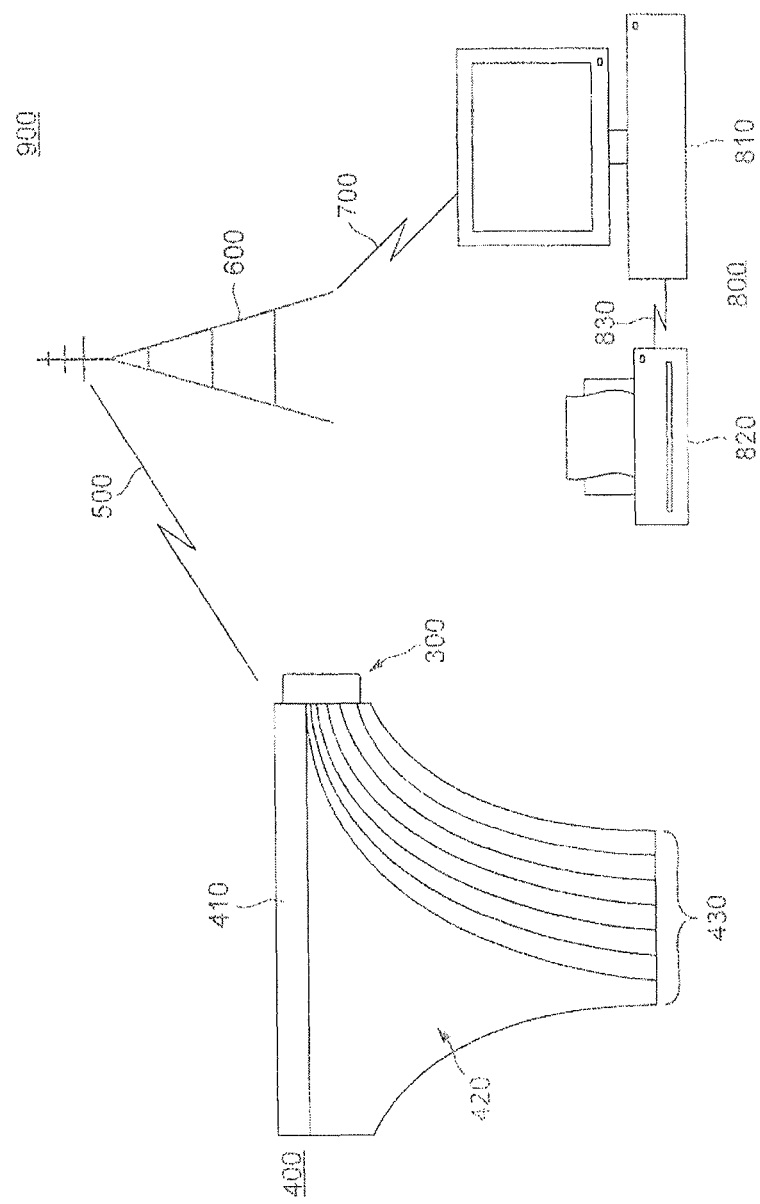
FIG. 1 is a schematic diagram of a monitoring system for absorbent articles.

The configuration of the absorbent article and monitoring system of the present disclosure can be similar to that disclosed in the arrangement of FIG. 1. However, logger unit 300 is provided in a multi-part form, for example a two-part form as shown in FIG. 2.

Figure 2:
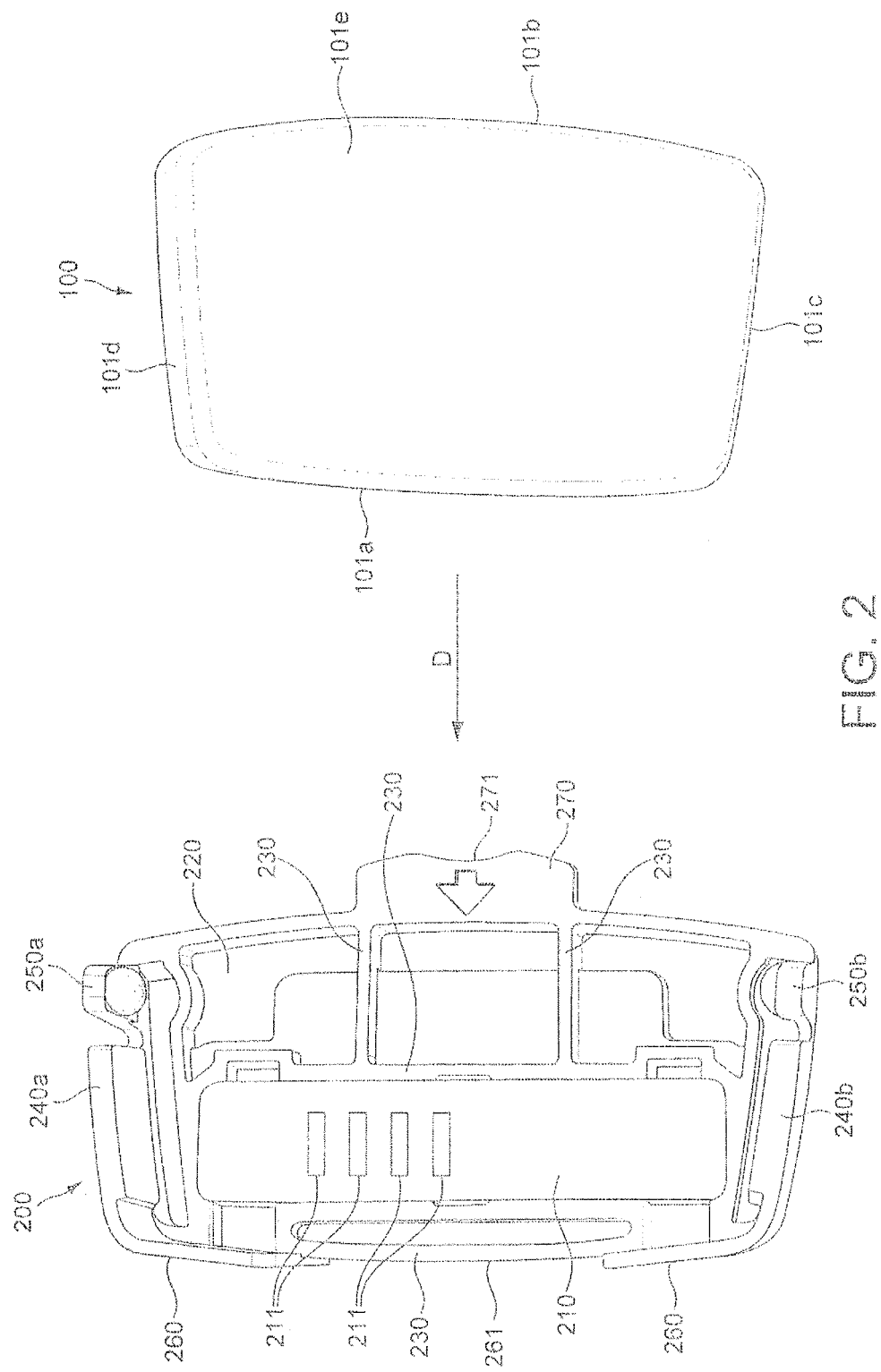
FIG. 2 is a top view of an enclosure and a receptacle each being an example of the present disclosure.

FIG. 2 shows enclosure 100 and corresponding receptacle 200. Enclosure 100 houses the electronics for monitoring the sensors 430, while receptacle 200 provides a point of attachment for the enclosure 100 for releasably attaching the enclosure 100 to the absorbent article 400. The electronics, here, may include a power source, processor, memory, instruction store, data store, communications bus, and data link interface, which cooperate to store, process, and/or forward the data derived from sensor wires. To facilitate this, the sensors 430 are arranged to terminate in electrical contacts 211 at a termination zone 210 of receptacle 200, at which the sensor wires 430 are terminated at electrical contacts. Enclosure 100 is provided with corresponding contacts such that when enclosure 100 is engaged with receptacle 200, the contacts of receptacle 200 come into electrical contact with the contacts of enclosure 100. Thus, when engaged in the receptacle 200, electronics enclosure 100 are able to communicate with the sense wires 430. Termination zone 210 can provide a substrate to support the contacts, or can be an open region to allow predefined contacts formed in the fabric of the absorbent article to protrude into the receptacle.

Receptacle 200 and enclosure 100 also provide a corresponding guide and engagement means, such that enclosure 100 may be easily introduced to and securely retained within receptacle 200. Features, described below, are also provided to enable the enclosure 100 to be released from the receptacle 200 by the user in a convenient manner, for example one-handedly. This is particularly important in institutional settings, since the user may not be compliant with the directions of the carer, and therefore it is advantageous for the enclosure 100 to be as easy as possible to correctly engage with and be released from the receptacle 200, even without the user needing to look at the receptacle or the enclosure. Allowing one-handed engagement and disengagement permits the other hand of the carer to be free to perform other tasks, for example in record-keeping or in encouraging user compliance.

Figure 3:
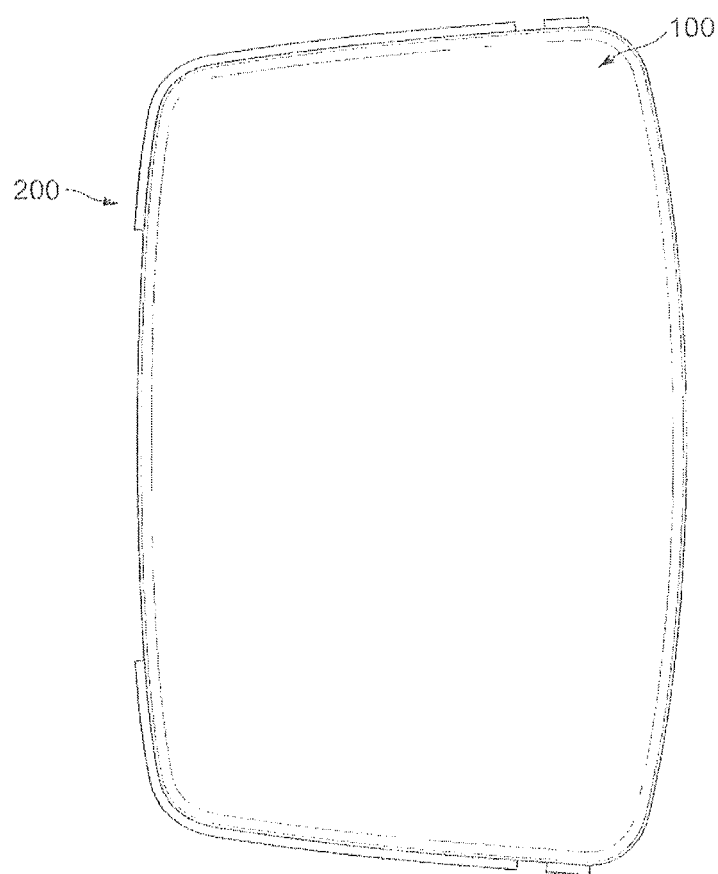
FIG. 3 is a top view of an enclosure engaged with a receptacle, each being an example of the present disclosure.
Figure 4:
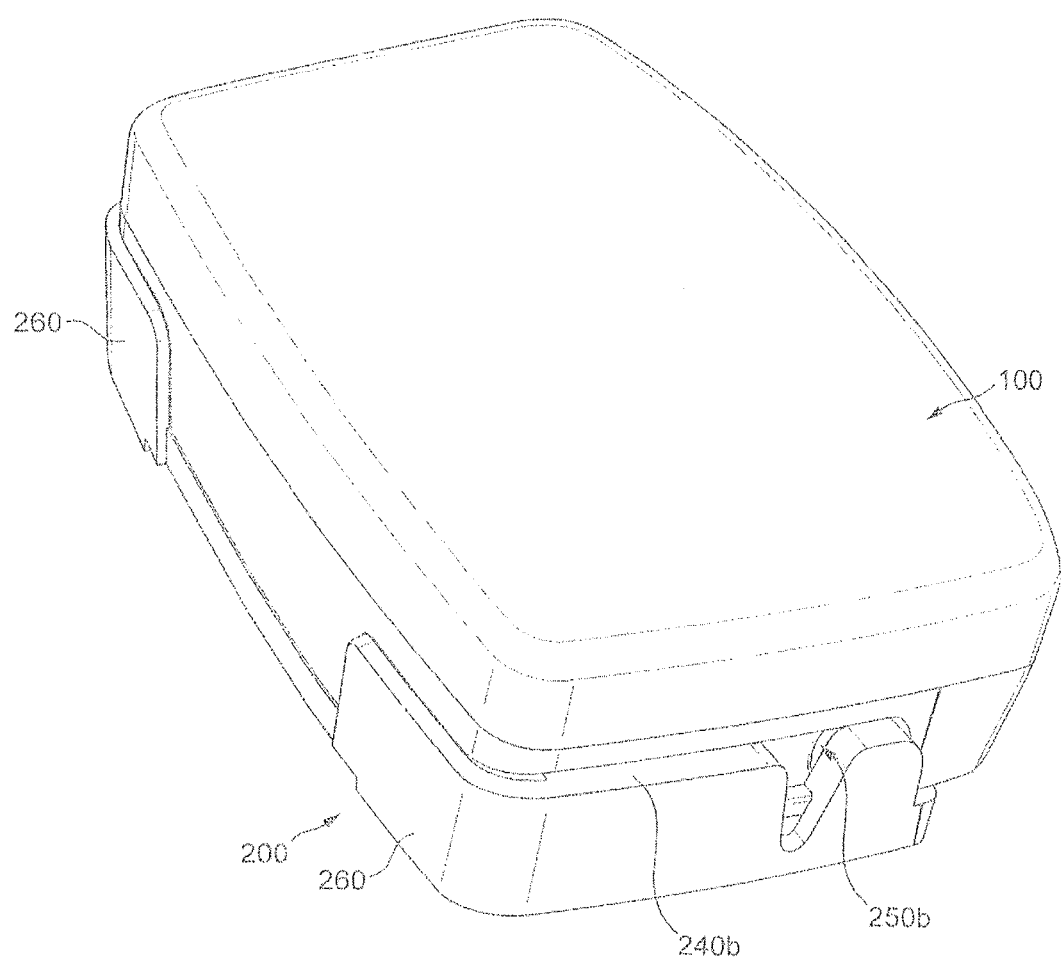
FIG. 4 is a front three-quarter view of an enclosure engaged with a receptacle, each being an example of the present disclosure.
Figure 5:
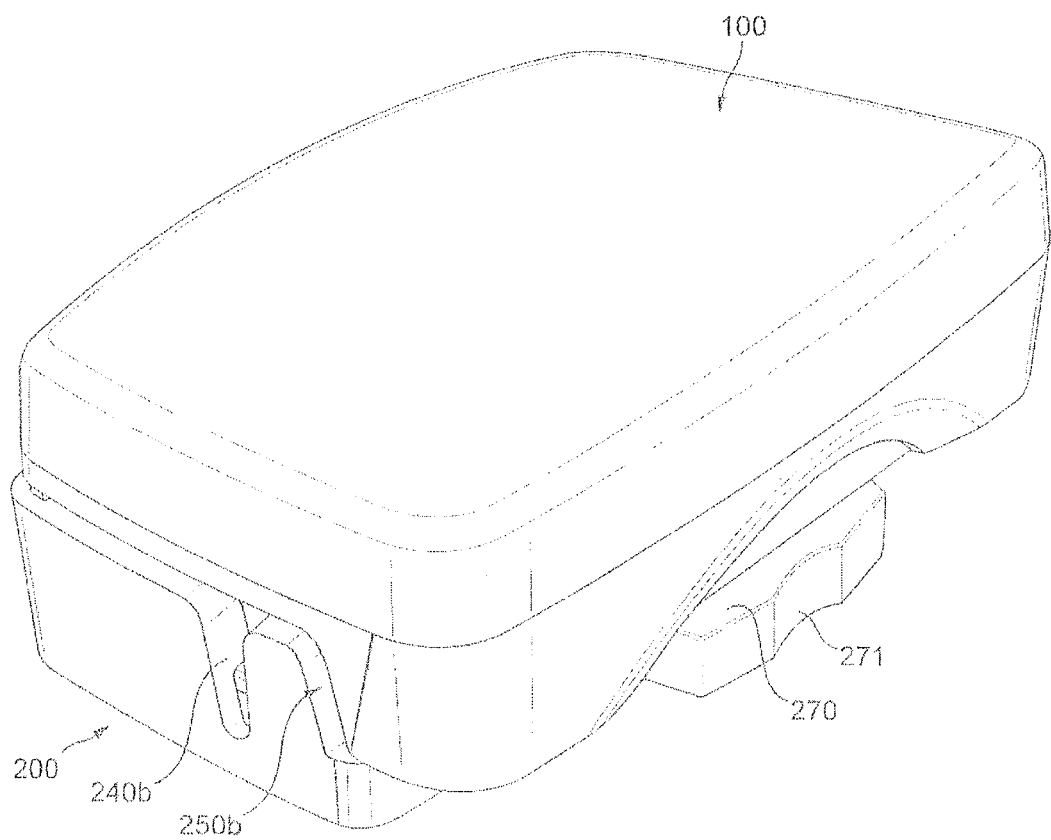
FIG. 5 is a rear three quarter view of an enclosure engaged with a receptacle, each being an example of the present disclosure.

The engaged configuration of the enclosure 100 with receptacle 200 is shown in greater detail in FIGS. 3, 4 and 5. To achieve the engaged configuration, the enclosure 100 is appropriately oriented and aligned with the receptacle 200 and is then translated in an engagement direction (shown in FIG. 2 as direction D) towards the receptacle until engagement is achieved, resulting in an engaged configuration (shown in FIGS. 3, 4 and 5). Various features of both the enclosure 100 and the receptacle 200 cooperate to permit such an engagement process, and its reverse disengagement process, to be both convenient and reliable, as more fully described with reference to each advantageous feature below.

Figure 6:
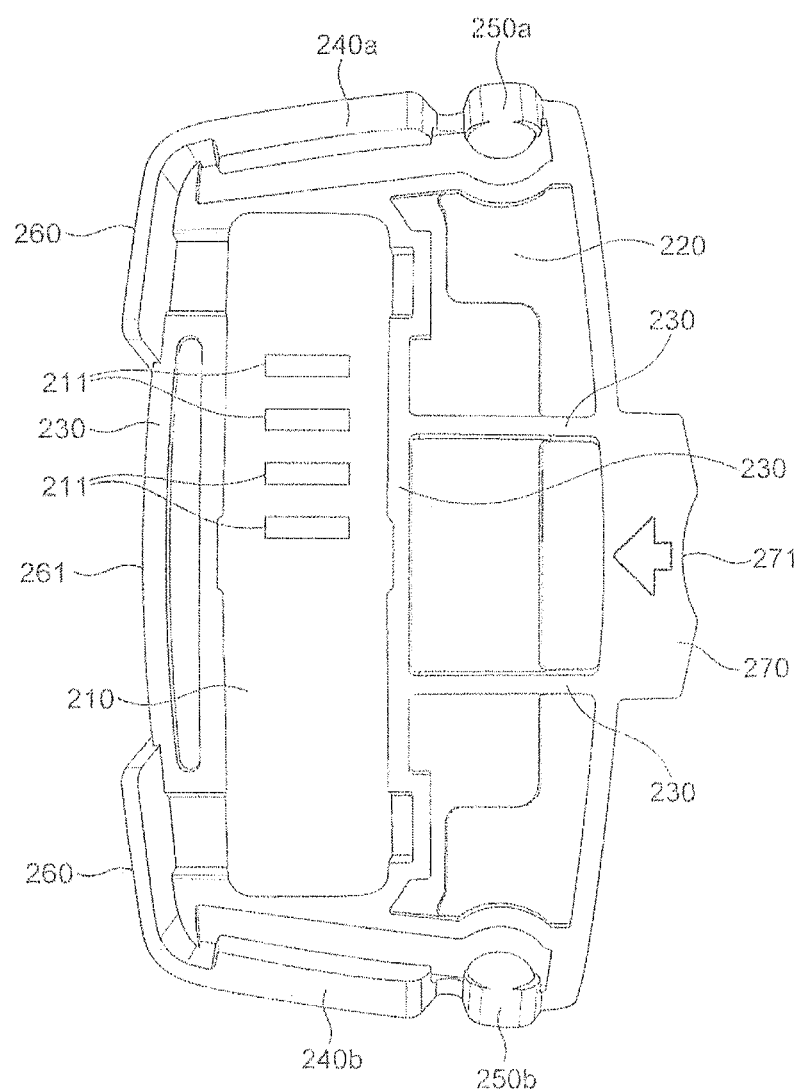
FIG. 6 is a top view of a receptacle being an example of the present disclosure.

FIG. 6 shows the receptacle 200 alone. Receptacle 200 has a base surface 220 along which a surface of the enclosure 100 can translate in the engagement direction to achieve an engaged configuration. The base surface 220 defines a plane in which the engagement direction lies, and during the engagement process constrains the position of the enclosure relative to the receptacle 200 to motion in that plane, hereinafter termed the engagement plane. The base surface can be planar and continuous, although in the arrangement of FIG. 6 the base surface is defined by the upper surface of ribs 230, between which are depressed areas to reduce the mass of the receptacle 200 and to provide an aperture for termination zone 210. Ribs 230 extend upwards from an essentially flat plate defining a lower absorbent-article-facing surface of the receptacle. However, in other configurations, different configurations of base surface, such as a planar continuous base surface, are possible.

The lower surface of the receptacle, in the present embodiment, the opposite side of the flat plate to the base surface, is here suitable to be provided with an adhesive patch to enable the receptacle to be fixedly attached to a surface of the absorbent article. This is, however, purely exemplary, and other fixing means such as hook-and-eye fasteners or holes for threads or rivets may be contemplated to attach the receptacle to the absorbent article. When an adhesive patch is used to fix the receptacle to the absorbent article, the receptacle may be provided with the adhesive patch for fixing the receptacle to the absorbent article at the time of manufacture, for example by applying an adhesive patch with an absorbent-article-facing surface covered by release paper, or the adhesive may be applied subsequently, at the point at which the receptacle is provided to the absorbent article, for example as a spray or liquid.

Figure 7:
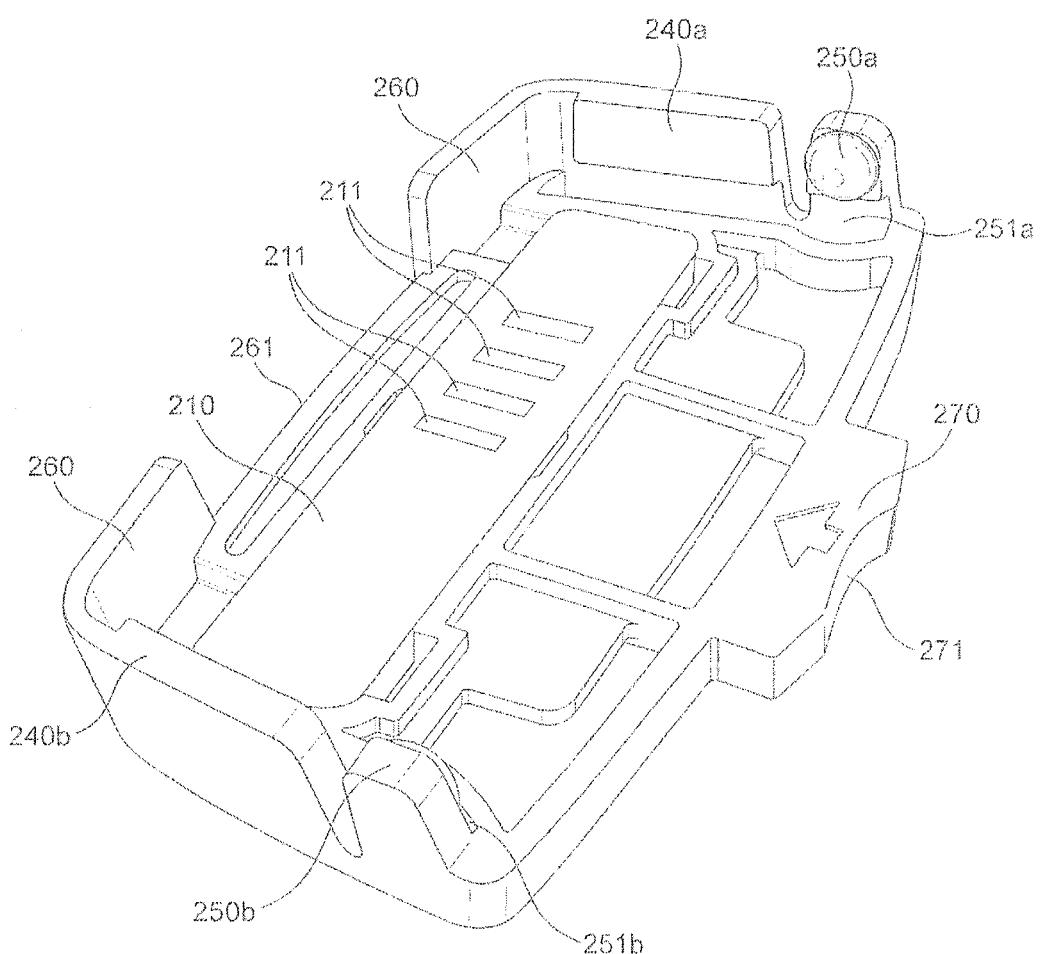
FIG. 7 is a rear three-quarter view of a receptacle, being an example of the present disclosure.
Figure 8:
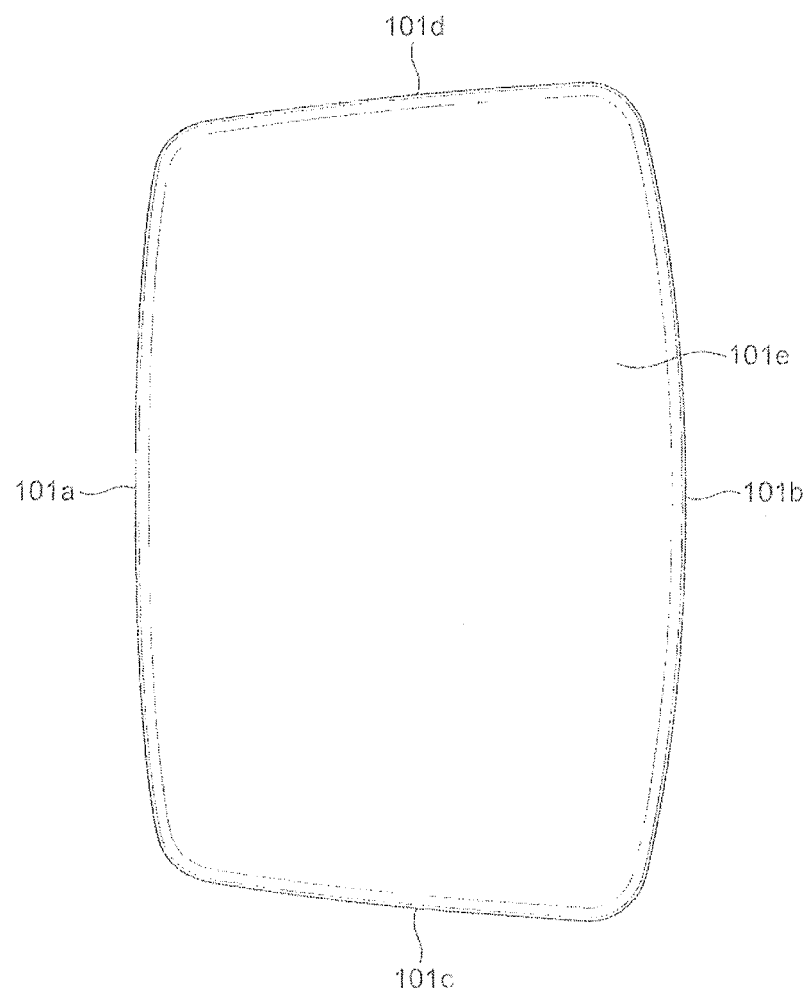
FIG. 8 is a top view of an enclosure being an example of the present disclosure.
Figure 9:
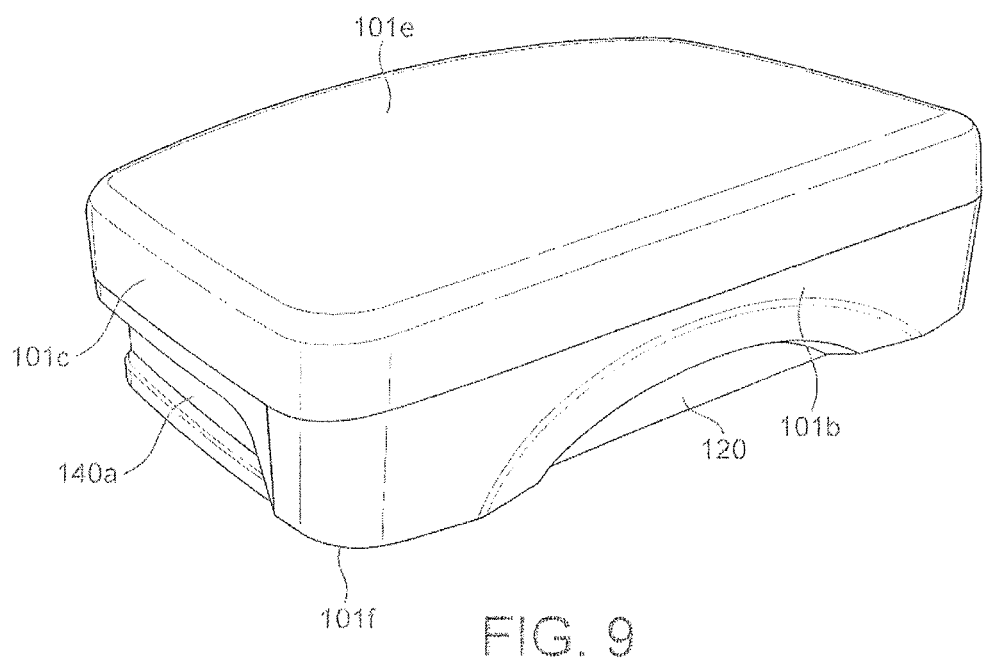
FIG. 9 is a front three-quarter view of an enclosure being an example of the present disclosure.
Figure 10:
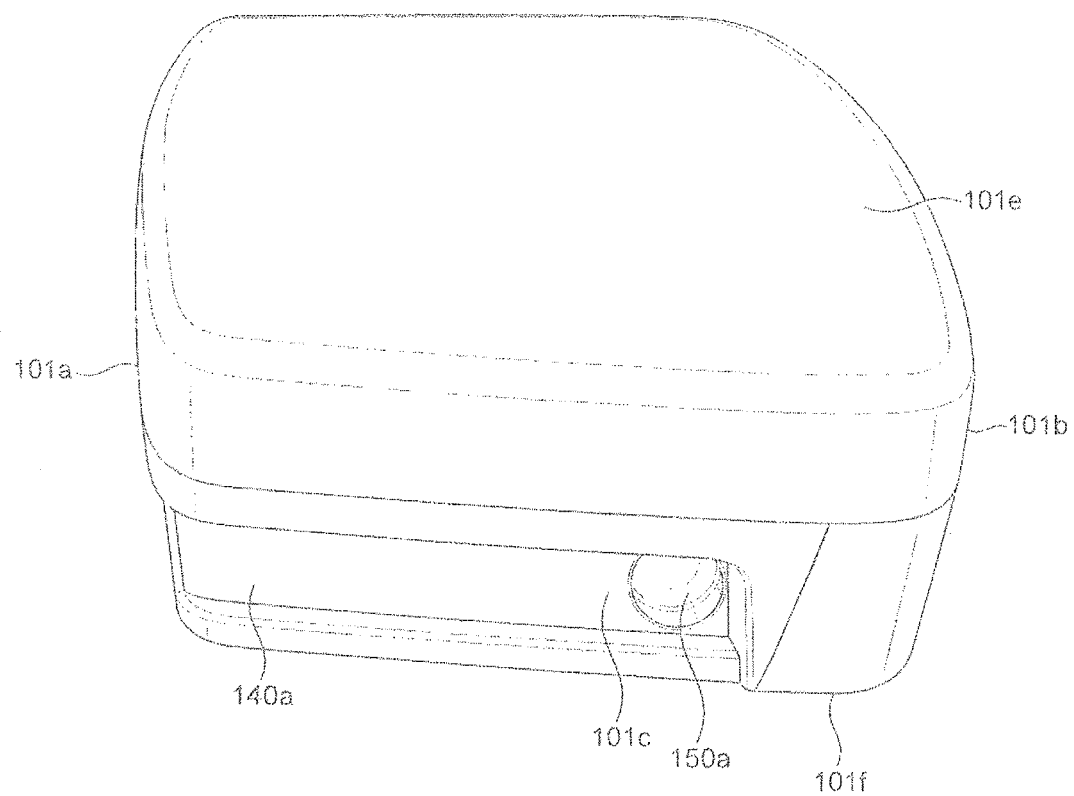
FIG. 10 is a side view of an enclosure being an example of the present disclosure.
Figure 11:
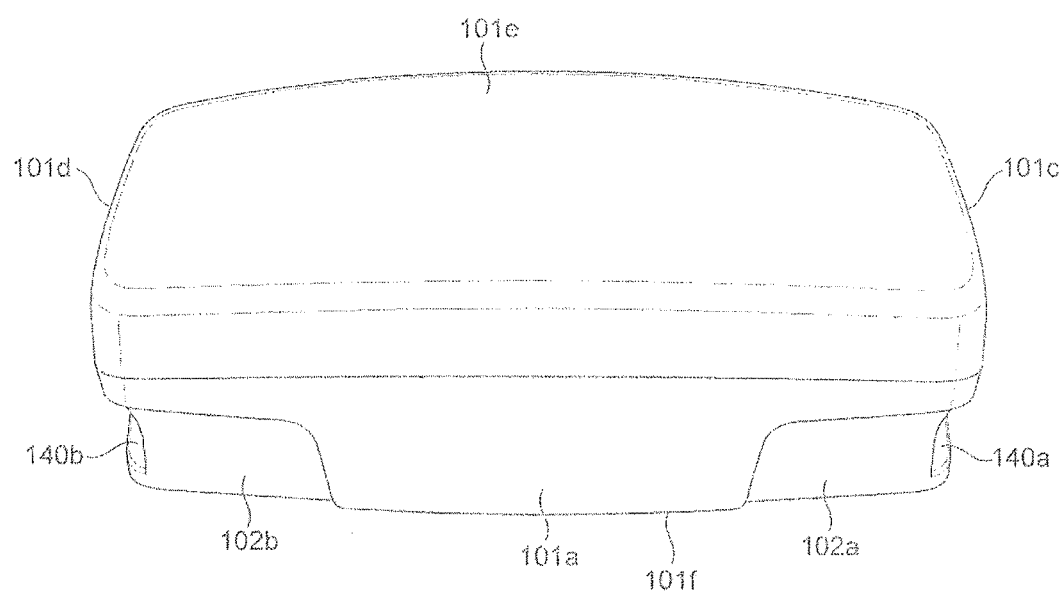
FIG. 11 is a front view of an enclosure being an example of the present disclosure.
Figure 12:
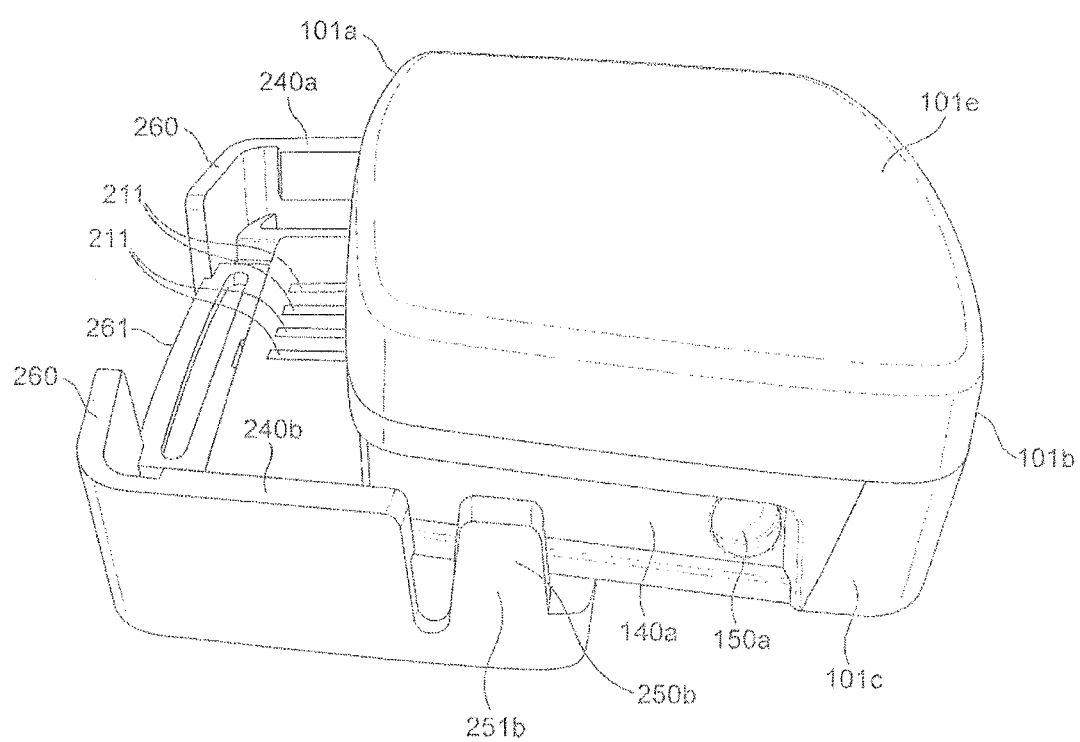
FIG. 12 is a side view of an enclosure and a receptacle, each being an example of the present disclosure, in a partially-engaged state.

The receptacle 200 is also provided with features which enable the motion of the enclosure 100 relative to the receptacle 200 within the engagement plane to be restricted further. Particularly, receptacle 200 has guide rails 240a, 240b, extending inwardly from side walls of the receptacle in a plane parallel to the engagement plane on opposite sides of the base plane. These rails 240a, 240b, as most clearly may be seen in FIG. 7, are raised above the base plane in a direction perpendicular to the base plane, supported by the side walls, and are arranged to cooperate with corresponding guide grooves 140a, 140b in the enclosure 100. The provision of guide rails 240a, 240b restricts rotation about the engagement direction, rotation about directions perpendicular to the engagement direction, as well as translation in the plane perpendicular to the engagement plane. The use of guide grooves and rails also permits initial misalignment, especially with regard to rotation of the enclosure 100 about an axis in the engagement plane but perpendicular to the engagement direction, to be smoothly corrected as the enclosure 100 and the receptacle 200 are brought into engagement. This is especially advantageous for enabling one-handed engagement, as the smooth correction of the direction of travel to the engagement direction is communicated to the carer as a gentle reorientation of the enclosure, as it is moved, into an orientation suitable for secure engagement.

The guide rails 240a and 240b are inclined relative to each other while remaining parallel to the engagement plane. Specifically, they are inclined such that they tend to converge in the engagement direction, such that the guide rails 240a, 240b are closer together at each of their ends which are more advanced in the engagement direction and the opposite ends of rails 240a, 240b, which are positioned rearwardly in the engagement direction, are relatively more separated. An effect of this relative inclination is that the guiding effect of the rails is progressively applied, such that an initial slight misalignment does not prevent engagement with the rails, but that as the enclosure 100 and the receptacle 200 are brought together into engagement, the guiding effect of the rails progressively increases to ensure that correct alignment is achieved during the more critical final phases of engagement.

The receptacle 200 is also provided with locking protrusions 250a, 250b, which are arranged to engage with corresponding locking depressions 150a, 150b on the enclosure 100. In the present embodiment, the projections 250a, 250b are formed in the manner of an extension of rails 240a, 240b in the direction opposite to the engagement direction and separated from the rails by a small spacing. The projections 250a, 250b are elevated above the base surface 220 in a direction perpendicular to the base surface by respective resilient portions 251a, 251b, formed as portions of the side walls of the receptacle, which enable each locking protrusion to flex inwardly and outwardly in a plane perpendicular to the engagement plane. Such a configuration reduces stress in the receptacle 200 and permits the locking protrusions 250a, 250b to snap into engagement with the corresponding lock depressions 150a, 150b once engagement is reached. The snap locking action indicates in a tactile manner to the carer that secure engagement, and thus adequate electrical connection between the contacts, is achieved, and also acts as a deterrent to further forward motion in the engagement direction.

Receptacle 200 also has a forward barrier 260 at a forward edge of the base surface 220 in the engagement direction, in the form of wall 260 extending upwardly from the base surface in a direction perpendicular to the engagement plane. In the present embodiment, wall 260 is integrally formed with the side walls bearing rails 240a, 240b. This wall 260 acts as a further stop on further forward movement of the enclosure 100 in the receptacle 200 once the engagement position has been reached, if the snap locking action of the locking protrusions 250a, 250b into depressions 150a, 150b is disregarded. Wall 260 also provides a barrier against external force being inadvertently applied to the enclosure 100 in a direction opposite to the engagement direction, i.e. a disengagement direction, causing the enclosure to become disengaged.

Wall 260 has a lowered portion 261 to provide limited access to a front surface of the enclosure 100 in a direction opposite to the engagement direction so that intentional force can be applied, for example by the thumb of a user or a carer, to the enclosure 100 while engaged with receptacle 200 to enable the enclosure 100 to become disengaged from the receptacle 200. Provided at an opposite edge of base surface 220 to wall 260, namely at a rear surface of base surface 220 with respect to the engagement direction, is projection 270 having grip depression 271. Projection 270 extends rearward from the rear surface of base surface 220 and provides a location where a user or carer can place an opposed finger, such as an index finger, so that with thumb pressure on enclosure 100 at a position exposed by lowered portion 261 of wall 260, relative force in a direction opposed to the engagement direction can be applied between the receptacle 200 and the enclosure 100, thereby to disengage receptacle 200 and enclosure 100.

Of course, there are many aspects of receptacle 200 which are optional, or which may be varied depending on need. For example, wall 260 and projection 270 may be absent, if it is not feared that the receptacle and the enclosure are likely to be subject to disengaging forces while in use. The guides 240b and 240a need not be relatively inclined, if it can be assumed that the user is able to align the enclosure and the receptacle appropriately for engagement. Indeed, guide rails 240a, 240b can be absent, and locking protrusions 250a, 250b and base surface 220 can alone be relied upon to guide the enclosure in the engagement plane. Alternatively, locking protrusions 250a, 250b can be absent, can be provided elsewhere, or can be replaced by other engagement means, e.g., catches or clips. The locking protrusions 250a, 250b could alternatively be provided on base surface 220 or on a surface opposed to base surface 220, thereby to form an enclosed receptacle on at least four sides. However, the described arrangement is considered advantageous in allowing the protrusions to perform an initial guiding function which facilitates one-handed operation.

Indeed, if a second surface positioned above base surface and oriented substantially parallel to the engagement plane were provided, guide rails 240a and 240b, as well as the walls supporting them, could be omitted, as this surface could then be used to guide the enclosure 100 into proper engagement with receptacle 200. Alternatively, rather than having locking protrusions 250a, 250b, locking depressions can be provided for corresponding locking protrusions on the enclosure. In some cases, it is preferred that the depressions or protrusions are provided forwardly of guide rails 240a, 240b, if present, in the engagement direction, rather than being positioned rearwardly as the locking protrusions 250a, 250b. Either configuration may be designed such that the locking effect is achieved only once the final, stable, engagement position is obtained.

Rails 240a, 240b need not be relatively inclined, although such inclination is presently considered advantageous. Indeed, base surface 220 need not be planar, but could be curved upwardly or downwardly in cross-section, looking along the engagement plane in the engagement direction. Such a surface will still restrict motion to an engagement plane, providing that a co-operating lower surface is provided to the enclosure. All such variants are considered to be within the scope of the present disclosure.

A corresponding exemplary enclosure 100 for use with the receptacle 200 is shown in FIGS. 8 to 11.

The depicted enclosure 100 has six surfaces which together define a housing for electronics to be enclosed therein. The first and second surfaces 101a and 101b, respectively, are front and rear surfaces in an engagement direction of enclosure 100 with receptacle 200. Third and fourth surfaces 101c, 101d are respectively left and right surfaces looking in an engagement direction of the enclosure 100 with the receptacle 200, with a horizon of view being defined as the engagement plane. Fifth and sixth surfaces are then top and bottom surfaces 101e, 101f, separated from one another in a direction perpendicular to the engagement plane. Left and right surfaces 101c, 101d are separated from each other in a direction perpendicular to the engagement direction but lying within the engagement plane.

In the present embodiment, enclosure 100 has top and bottom surfaces 101e, 101f, which are generally in the shape of isosceles trapezoids, at least in terms of their substantial perimeter. However, in clinical environments, it is advantageous that sharp edges are avoided, as they can provide difficulty in cleaning and problems in user comfort, and therefore at least front and rear surfaces 101a, 101b, are respectively bowed outward in a direction respectively toward and opposed to the engagement direction. Therefore, at least the parallel sides of the isosceles trapezoid defining the perimeter of top and bottom surfaces 101e, 101f are not strictly parallel, but rather are also slightly bowed outwardly in a corresponding fashion. In the present enclosure 100, bottom surface 101f is planar and flat, to easily translate across, in a sliding fashion, base surface 220 of receptacle 200. In contrast, top surface 101e is not, as such, planar, but is slightly bowed outward in a direction perpendicular to the engagement plane. The planes defined by each of the perimeters of top surface 101e and bottom surface 101e are here parallel, but could be inclined such that they tend to converge in a given direction, such as the engagement direction, disengagement direction, or a direction perpendicular to the engagement direction.

As a consequence of the substantially isosceles trapezoidal configuration of top and bottom surfaces 101e, 101f, left and right surfaces 101c, 101d are mutually inclined such that the forward edges of left and right surfaces 101c, 101d are relatively closer together than the rearward edges of left and right surfaces 101c, 101d relative to the engagement direction. As a consequence of this inclination, and also as a consequence of the different radius of curvature of top surface 101e relative to bottom surface 101f, it is easy for a user, holding receptacle 200, to determine by touch alone the orientation of enclosure 100, and to correctly orient it for engagement with receptacle 200, without the necessity of looking at the enclosure 100. This is of advantage when the receptacle is positioned at a location where the user or the carer cannot easily see, such as at a rear waistband of a diaper, or where the carer or user is also performing some other task, such as fastening a diaper, or making written records, at the same time as engaging the enclosure 100 with the receptacle 200.

However, the configuration shown in the Figures is not the only way of achieving this arrangement, and it is considered that it is easy for a carer to determine the orientation of the enclosure for engagement with a corresponding receptacle provided that the housing has no more than one plane of symmetry which includes the engagement direction. The asymmetry may be provided in a variety of ways. For example, the converging left and right walls and the distinct curvatures shown in the Figures is considered advantageous, but providing the surfaces with distinct textures or relief patterns, or providing other such asymmetric features, is also considered to enable this configuration. Particularly, geometric asymmetric rather than textural or surface asymmetry is considered to be of particular advantage of assisting the carer in engaging an enclosure with a receptacle. An alternative asymmetry which could be employed is by providing top and bottom surfaces 101e, 101f, which, although trapezoidal, are not isosceles, or which are not even trapezoidal, none of the edges even being approximately parallel. Other features contributing to the lack of symmetry include the provision of guide grooves 140a, 140b which extend only partly along respective sides 101c, 101d of enclosure 100 and relatively closer to bottom surface 101f than top surface 101e, allows a user to easily determine, by touching only those sides, the orientation of the enclosure. However, the present embodiment is easy to use but sufficiently asymmetric as to enable easy engagement with the receptacle.

Bottom surface 101f is provided with a contact zone (not shown) having electrical contacts. These contacts are positioned so as to be in electrical contact with the corresponding contacts in the receptacle, when the enclosure 100 is engaged with the receptacle. In particular embodiments, these contacts are positioned relatively forwardly on the enclosure in the engagement direction, which ensures that the electrical contact is not made until the enclosure 100 is firmly engaged in receptacle 200. In particular embodiments, the positioning and/or length in the engagement direction of each of the contacts of the enclosure and the contacts of the receptacle is such that the snap feedback between the locking protrusions and locking depressions only occurs once the respective sets of contacts are in secure electrical contact. In one embodiment, this can be achieved by ensuring that the length in the direction opposite to the engagement direction of at least one of the contacts of a pair of corresponding contacts on the receptacle and enclosure respectively, measured from a point of electrical contact with the corresponding contact in the engagement position, is greater than half the length of the locking protrusion in the engagement direction, and, in certain embodiments, greater than the whole length of the locking protrusion. However, positionings for the contacts other than at base surface 101f may be contemplated. For example, the contacts could be formed on front surface 101a for engagement with corresponding contacts formed, for example, on front wall 260 of enclosure 200.

Left and right surfaces 101c, 101d are respectively provided with guide grooves 140a, 140b, extending from the front surface 101a at least partially rearwardly along left and right surfaces 101c, 101d, in the engagement plane. In particular embodiments, the guide grooves 140a, 140b open at the front surface 101a, although this is not strictly necessary if left and right surfaces 101c, 101d are sufficiently inclined as to permit corresponding guide rails 240a, 240b provided to receptacle 200 to engage with the guide grooves 140a, 140b at an initial engagement position rearward of front surface 101a. In the present embodiment of the enclosure 100, locking depressions 150a, 150b are provided in and at a rear end of guide grooves 140a, 140b, respectively, for engagement with locking protrusions 250a, 250b of the receptacle. This positioning is advantageous, since it enables the locking protrusions to contribute to the guiding effect of guide rails 240a, 240b travelling in guide grooves 140a, 140b, and, together with the inclination of the left and right surfaces 101c, 101d to each other, permits a gradually increasing guiding and locking force to be applied respectively from guide rails 240a, 240b and locking protrusions 250a, 250b to the inner surfaces of guide grooves 140a, 140b as the enclosure 100 is translated in the engagement direction into the receptacle 200. In the present embodiment, the guide grooves 140a, 140b do not extend as far as rear surface 101b of enclosure 101, and each locking depression is at the rearmost position of the corresponding groove. This configuration allows the rear wall of the groove, i.e. the surface of the groove in a direction opposite to the engagement direction, to act as a stop against further motion of the enclosure in the engagement direction once the engagement configuration with the receptacle has been reached.

Two advantages of this arrangement in which the locking force is felt to progressively increase are firstly that it is relatively easy to initially engage the enclosure 100 with the receptacle 200 without having to overcome an initial large guide or locking force, and secondly the locking force applied by the locking protrusions 250a, 250b against the inner surfaces of guide grooves 140a, 140b progressively increases as the enclosure 100 is inserted into receptacle 200, thus providing feedback to the user, in the form of gradually increasing difficulty of insertion, that the engagement process is proceeding smoothly and correctly. This force is immediately relieved when the enclosure 100 is fully inserted into receptacle 200, when locking protrusions 250a, 250b snap from a relatively outwardly flexed position, adopted as locking protrusions 250a, 250b relatively slide rearwardly along guide grooves 140a, 140b, to an inward locking position, when the outward flexural force is relieved and the locking protrusions 250a, 250b settle in locking depressions 150a, 150b.

However, other configurations and locations of locking protrusions are contemplated, and indeed the locking protrusions could be provided to the enclosure, either on left and right surfaces 101c, 101d, or on, for example, top and bottom surfaces 101e, 101f, or the protrusions could be provided to the enclosure and the depressions could be provided to the receptacle. Indeed, the locking behaviour described does not rely on the left and right surfaces 101c, 101d being inclined relative to one another, and can be achieved with parallel left and right surfaces 101c, 101d, provided an initial force is overcome when inserting the enclosure 100 into the receptacle 200, in which front inner surfaces of guide grooves 140a, 140b, if present, or otherwise the left and right surfaces 101c, 101d, apply an outward force to corresponding locking protrusions 250a, 250b to outwardly flex the protrusions as the enclosure is inserted into the receptacle. Similar advantages can also be achieved with protrusions located on the enclosure and depressions located on the receptacle. However, forming the protrusions on the enclosure has an advantage that the protrusions are easier to clean in a hygienic setting than depressions. On the other hand, the alternative configuration in which the protrusions are located on the receptacle is advantageous in that the protrusions cooperate with the guide grooves to initially align the enclosure and receptacle for engagement.

Notably, the protrusions and depressions can be hemispherical or dome-shaped, to enable smooth engagement one with the other, although pyramidal, triangular prismatic, and other shapes of protrusion may be used, without limitation.

Figure 13:
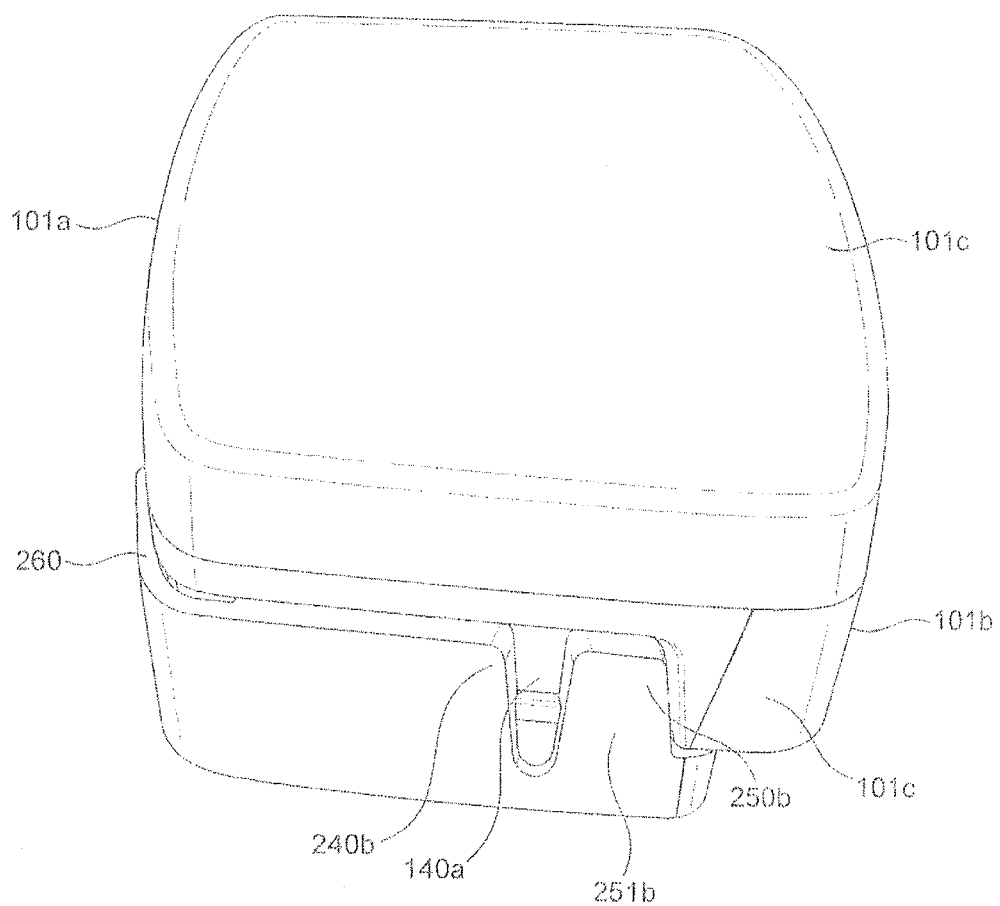
FIG. 13 is a side view of an enclosure and a receptacle, each being an example of the present disclosure, in a fully-engaged state.
Figure 15:
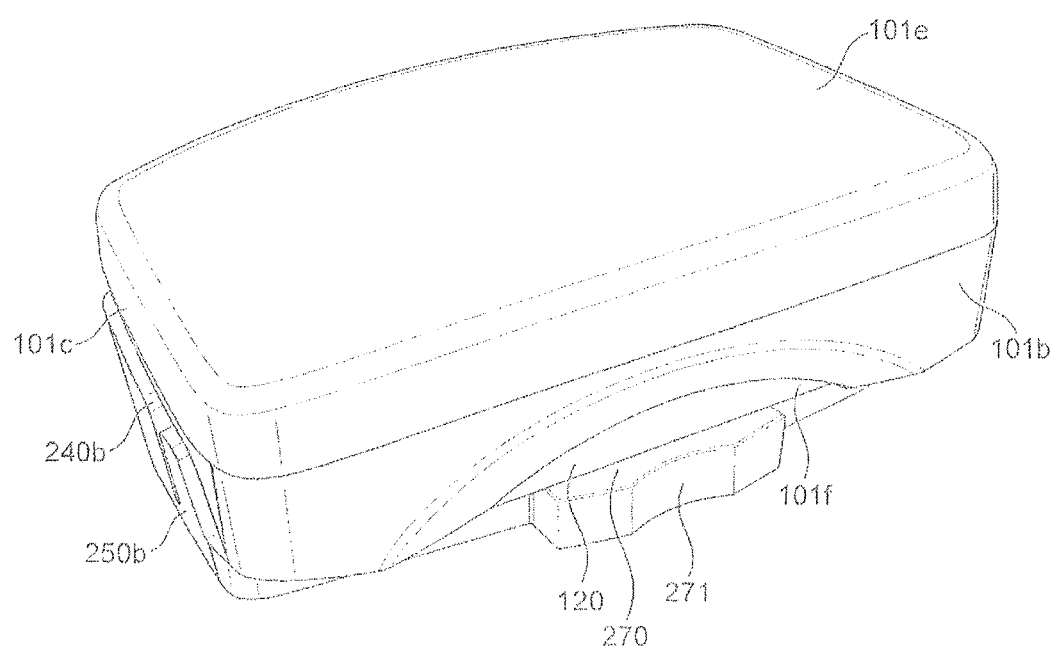
FIG. 15 is a rear three-quarter view of an enclosure and a receptacle, each being an example of the present disclosure, in a fully-engaged state.
Figure 16:
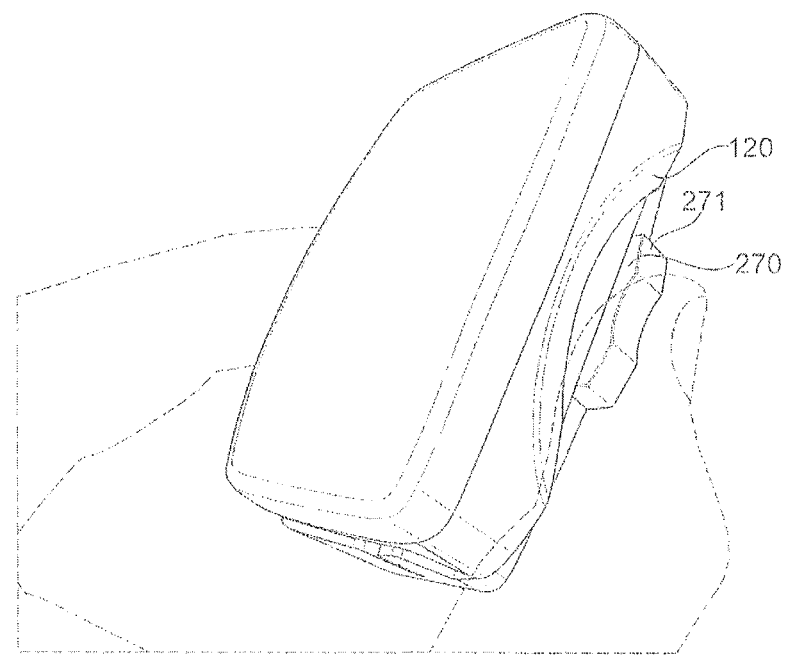
FIG. 16 is a first view of an enclosure and a receptacle, each being an example of the present disclosure, during a disengagement process.
Figure 17:
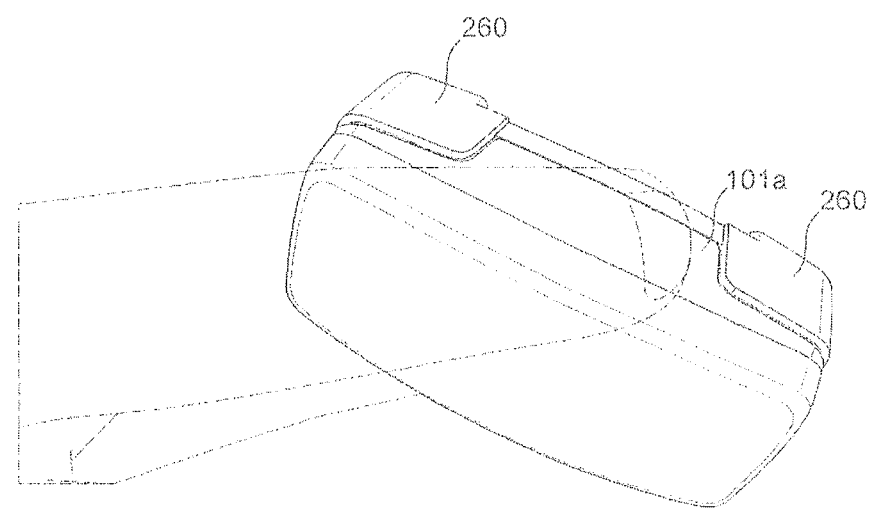
FIG. 17 is a second, alternative view of an enclosure and a receptacle, each being an example of the present disclosure, during the disengagement process.

Enclosure 100 is also provided with a depression on rear surface 101b extending to the edge at which rear surface 101b joins bottom surface 101f. Not only does this feature provide further asymmetry from front to rear, enabling correct orientation to be determined, but this feature also enables easy disengagement of the enclosure 100 from the receptacle 200. Starting from the engaged state shown in FIGS. 13, 14 and 15, and with particular reference to FIG. 15, it can be seen that depression 120 allows base surface 220 of receptacle 200 to extend beyond an edge at which rear surface 101b of enclosure 100 joins bottom surface 101f of enclosure 100 while preventing the base surface 220 as a whole from generally protruding beyond the rear surface of the enclosure 100 as a whole. This configuration permits intentional force to be easily applied by a user or carer between enclosure 100 and receptacle 200 in a direction opposed to the engagement direction while avoiding application of inadvertent force in that direction. By providing depression 120, the rear end surface of base surface 220 of receptacle 200 can be made accessible protruding beyond the inner surface of depression 120. Thus, for example, pressure can be applied with the thumb to end surface 271 of protrusion 270, which is also the rear-most surface of base surface 220, while the fingers apply an opposed force opposite to the engagement direction to front surface 101a of enclosure 100. As the pressure is applied, the enclosure 100 will translate relative to receptacle 200 in a direction opposed to the engagement direction, i.e., in the disengagement direction, as the protrusion 270 recedes below bottom surface 101f of enclosure 100. In particular embodiments, the depression 120 should extend sufficiently deeply relative to rear surface 101b that pressure can be applied to the end surface 271 of receptacle 200 until the locking protrusions 250a, 250b are completely disengaged from locking depressions 150a, 150b, at which point it is easy to slide the enclosure 100 away from receptacle 200 to completely disengage the two. This process of engagement and disengagement is shown in FIGS. 16 and 17. However, the depression 120 is not essential, and protrusion 270 can be provided on its own, or vice versa, to provide a location where force can be applied to separate receptacle 200 from enclosure 100.

Figure 14:
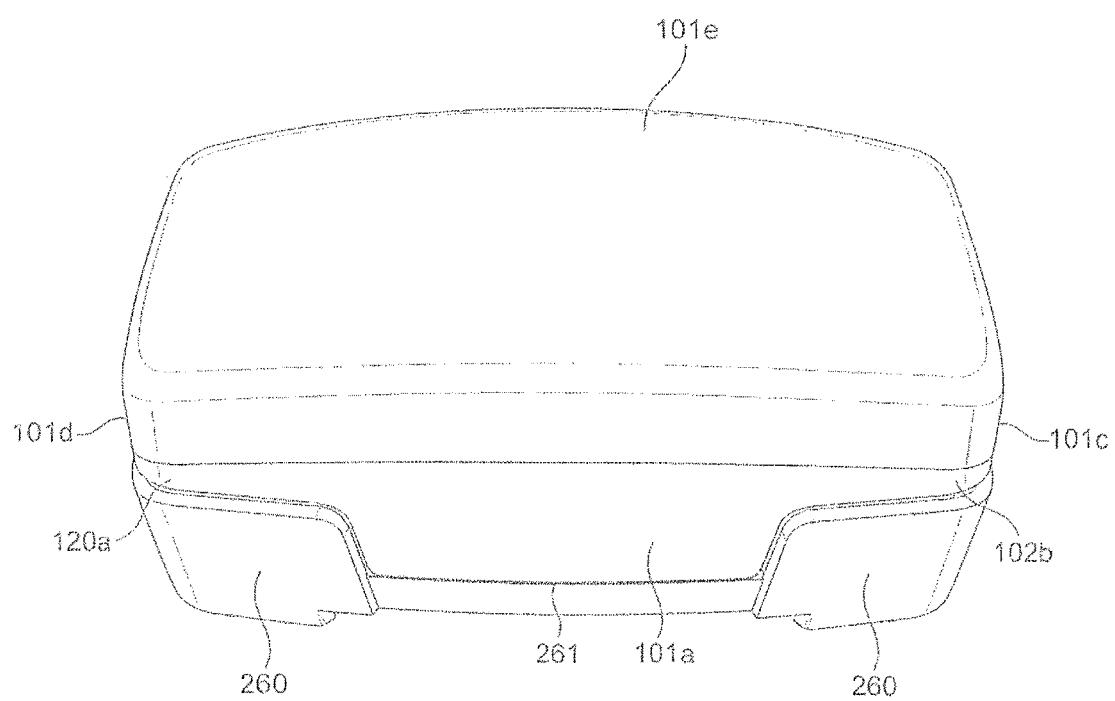
FIG. 14 is a front view of an enclosure and a receptacle, each being an example of the present disclosure, in a fully-engaged state.

With reference also to FIG. 16, and also to FIG. 14, lowered portion 261 of wall 260 of receptacle 200 is advantageous in facilitating this disengagement. By providing wall 260 with lowered portion 261, a space is provided such that force can be applied to front surface 101a of enclosure 100, for example by the finger, as shown in FIG. 16, during the disengagement process, while the remainder of wall 260 prevents inadvertent impacts on the front of the receptacle from causing inadvertent disengagement.

Advantageously, front surface 101a of enclosure 100 is provided with recesses 102a, 102b, which are shaped to accommodate the portions of wall 260 other than lowered portion 261 so that, when engaged in receptacle 200, front surface 101a of enclosure 100 and wall 260 presents an essentially smooth and uniform front surface. This has an advantage that users, who may be unfamiliar with the configuration of absorbent article, will not be encouraged to attempt to separate the enclosure 100 and receptacle 200 at an inappropriate time.

In the exemplary embodiment, both receptacle and enclosure are formed from ABS plastic, but the choice of material is essentially limited only by any local design constraints and the availability of materials.

In the exemplary embodiment, the first to sixth surfaces of the enclosure are whole surfaces bordered by edges, for example rounded edges, at which each surface meets others of the surfaces. However, the present invention is not limited to such a construction, and at least some of the advantages of the present invention can be obtained by embodiments having first to sixth surface portions, each of which may be part of a larger surface, and some or all of which may be contiguous and may be joined smoothly one to another without edges.

For example, if the third, fourth, fifth and sixth surface portions are contiguous, the third to sixth surface portions may form an arcuate surface, and the cross-section of the enclosure taken across the engagement direction may be substantially elliptical or circular. If the third, fourth and sixth surface portions are contiguous, but the fifth surface is planar, the third, fourth and sixth surface portions may form an arcuate surface and the cross-section of the enclosure may be a circular segment or semi-circular. If the fifth surface is planar but the third and fourth surfaces meet at an edge, an apicial surface, especially a rounded surface, of that edge may be regarded as a sixth surface portion joining the third and fourth surfaces, and the cross-section of the enclosure may be triangular. Other variants are possible, on such principles, and the present disclosure is intended as applicable to all such variants. For example, the cross-section may vary with length in the engagement direction.

FIG. 18A-D show, purely as examples of possible cross-sections: A an elliptical cross-section; B a rectangular cross-section having rounded corners; C a circular segment cross-section; and D a triangular cross-section.

Figure 18:
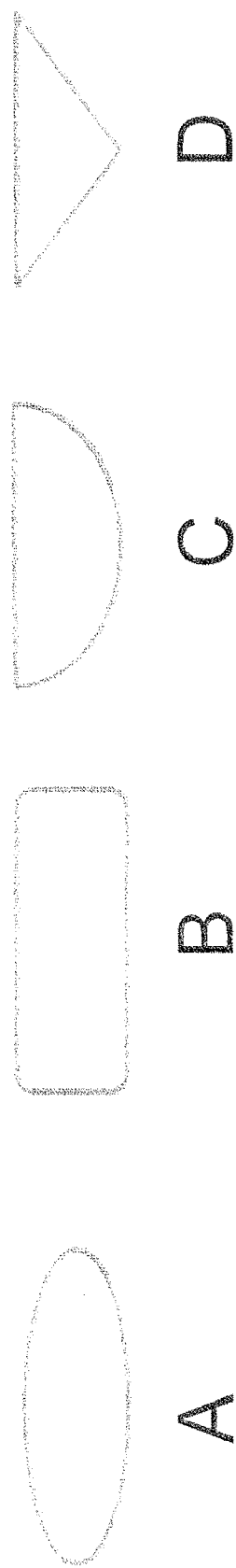
FIGS. 18A-D show cross-sectional shapes of variant embodiments of the disclosed enclosure.

With reference to FIG. 18A, and as an example only of the application of the principles of the exemplary embodiment previously described to the variants having alternative cross-sections, the guide grooves and locking depressions can be located at or near the ends of the major axis of the ellipse. In such a configuration, the electrical contacts may be provided at one (lower) end of the minor axis of the ellipse. However, this is only one possible configuration, and the guide grooves and locking depressions could be located at a position between the ends of the major and minor axes of the ellipse.

With reference to FIG. 18B, and again as an example only, the guide grooves and locking depressions can be located at or near the ends of the long axis of the rectangle. In such a configuration, the electrical contacts may be provided at one (lower) end of the short axis of the rectangle. However, this is only one possible configuration, and the guide grooves and locking depressions could be located at a position on the short sides of the rectangle other than the end of the long axis, while the electrical contacts could be located at a position on the short sides of the rectangle other than the end of the short axis.

With reference to FIG. 18C, and again as an example only, the guide grooves and locking depressions can be located on upper side portions of the curved surface of the segment. In such a configuration, the electrical contacts may be provided at the lowest point of the curved surface. However, this is only one possible configuration, and for example the electrical contacts could be located at a position part-way up the curved surface from the lowest point, while there is freedom as to where to position the guide grooves and locking depressions, depending on the radius of curvature selected.

With reference to FIG. 18D, and again as an example only, the guide grooves and locking depressions can be located on upper side portions of the sides of the triangle which are inclined to the horizontal. In such a configuration, the electrical contacts may be provided at one or both sides of the apex, or if the apex is rounded, spanning the apex.

However, as for the examples A, B and C, this is only one possible configuration, and again there is considerable freedom in locating the various elements of the exemplary embodiment.

Of course, for each variant enclosure, suitable straightforward modification of the receptacle, and in particular of the base surface, could be applied to allow close and secure engagement with the variant enclosure.

Now the configuration and mutual operation of enclosure 100 and receptacle 200 has been described, some advantages of their application to the system of FIG. 1 may become clear.

Particularly, the receptacle 200, which is relatively inexpensive and contains no electronics, may be provided as multiple instances to a series of diapers for use by one individual, while, in contrast to the system of FIG. 1, only one enclosure 100 is required, which is associated with a particular individual. During manufacture of each diaper 400, each receptacle 200 is attached at a convenient location and contacts of receptacle 200 are provided as terminations of sense wires 430.

Enclosure 100, on the other hand, encloses data-logging electronics such as a power source, processor, memory, instruction store, data store, communications bus, and data link interface, which cooperate to store, process, and/or forward the data derived from sense wires 430 via data link 500, data receiver 600, data link 700, to data processing equipment 800. Where the data link 500 is a wireless data link, such transmission can be immediate and on-demand, or delayed and batch transmitted to save power or communication costs. Where data receiver is a docking station, the logger electronics will typically store data for a time period before downloading it through the docking station.

Initially, a user is fitted with absorbent article 400 to which receptacle 200 is provided, and enclosure 100 containing the logger electronics is engaged with the receptacle. The contacts of receptacle and enclosure are thus brought into electrical connection, and the electronics in the enclosure are able to access the sense wires for logging purposes.

When it becomes apparent that the absorbent article should be replaced, the enclosure containing the logger electronics is easily removed by the carer or the user by means of the disengagement process previously described, the absorbent article is discarded, and a replacement absorbent article, with a replacement receptacle 200, is provided. The enclosure 100 containing the logger electronics associated with a particular user is then engaged with the new receptacle 200, according to the previously-described engagement process, and is connected thereby to the sense wires 430 of the new absorbent article 400. Therefore, data logging can continue with a single logger while the relatively inexpensive absorbent articles are used and discarded.

Therefore, a system of monitoring the status of a absorbent article associated with a user, and of monitoring the status even of several different absorbent articles associated with that user over time, becomes cost effective and convenient.

Such a system may find application in residential homes, medical facilities, child care facilities, schools, corrective facilities, and other environments where the monitoring of the continence status of one individual or a plurality of individuals is required.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. An electronics enclosure for engagement with a cooperating receptacle, comprising:
   terminal conductors for contacting corresponding conductors in the receptacle when engaged with the receptacle; and
   a housing having first, second, third, fourth, fifth, and sixth surface portions arranged to define the exterior of the housing,
   wherein the first and second surface portions are respectively front and rear surface portions in an engagement direction of the enclosure with the receptacle,
   wherein the third and fourth surface portions each connects the first and second surface portions,
   wherein the fifth and sixth surface portions each connects the first and second surface portions and each connects the third and fourth surface portions and are spaced apart in a direction other than the engagement direction,
   wherein the housing has no more than one plane of symmetry which includes the engagement direction, and
   wherein the fifth surface portion is configured to support the terminal conductors and the sixth surface portion has a radius of curvature smaller than that of the fifth surface portion in a plane perpendicular to the engagement direction.

2. The electronics enclosure according to claim 1, wherein the third and fourth surface portions each includes one of a locking protrusion and depression configured to engage a corresponding element of the receptacle to retain the enclosure within the receptacle.

3. The electronics enclosure according to claim 1, wherein the housing has a depression on an edge joining the rear and lower surface portions and extending at least partly across those surface portions from the edge.

4. The electronics enclosure according to claim 1, wherein the third and fourth surface portions are relatively inclined to approach each other in the engagement direction from the second to the first surface portion.

5. The electronics enclosure according to claim 1, wherein the third and fourth surface portions are each provided with a groove or rail configured to engage a retaining portion of the receptacle and extending at least partly along each surface portion from the first surface portion to the second surface portion.

6. The electronics enclosure according to claim 5, wherein a locking depression or projection is configured to engage a corresponding element of the receptacle to retain the enclosure within the receptacle and is located at the groove or rail.

7. The electronics enclosure according to claim 5, wherein each groove or rail is provided parallel to an edge joining the respective third or fourth surface portion to the fifth surface portion.

8. The electronics enclosure according to claim 5, wherein each groove or rail is provided relatively closer to an edge joining the third or fourth surface portion, respectively, to one of the fifth and sixth surface portions than to an edge joining the third or fourth surface portion, respectively, to the other of the fifth and sixth surface portions.

9. The electronics enclosure according to claim 1, wherein the fifth and sixth surface portions have different radii of curvature in a plane perpendicular to the engagement direction.

10. The electronics enclosure according to claim 1, wherein at least one pair of surface portions, selected from the group consisting of: i) the pair of the third and fourth surface portions; and ii) the pair of the fifth and sixth surface portions, are provided with texture that differs one from the other.

11. The electronics enclosure according to claim 1, wherein the fifth surface portion is substantially planar.

12. The electronics enclosure according to claim 1, wherein the fifth and sixth surface portions have perimeters which are isosceles trapezoidal.

13. The electronics enclosure according to claim 1, wherein the second and third surface portions have perimeters which are rectangular.

14. The electronics enclosure according to claim 1, wherein the enclosure has rounded corners where the sixth surface portion meets at least any two of the first to fourth surface portions.

15. The electronics enclosure according to claim 1, wherein at least one of the first and second surface portions are curved outwardly in a direction respectively along or opposed to the engagement direction.

16. The electronics enclosure according to claim 1, wherein the sixth surface portion is curved outwardly in a direction perpendicular to the engagement direction.

17. The electronics enclosure according to claim 1, wherein the enclosure contains logging electronics connected to the terminal conductors and configured to receive and process sensor signals from an absorbent article via the terminals conductors.

18. An electronics enclosure for engagement with a corresponding receptacle, comprising:
   enclosure terminal conductors for contacting corresponding receptacle terminal conductors in the receptacle when engaged with the receptacle; and
   a housing having first, second, third, fourth, fifth and sixth surface portions arranged to define the exterior of the housing,
   wherein the first and second surface portions are respectively front and rear surface portions in an engagement direction of the enclosure with the receptacle,
   wherein the third and fourth surface portions each connects the first and second surface portions,
   wherein the fifth and sixth surface portions each connects the first and second surface portions and each connects the third and fourth surface portions and are spaced apart in a direction other than the engagement direction, and
   wherein the third and fourth surface portions each is provided with a locking depression or projection configured to engage a corresponding portion of the receptacle to retain the enclosure within the receptacle.

19. The electronics enclosure according to claim 18, wherein the housing has no more than one plane of symmetry which includes the engagement direction.

20. The electronics enclosure according to claim 18,
   wherein the fifth surface portion is configured to support the enclosure terminal conductors and the sixth surface portion has a radius of curvature smaller than that of the fifth surface portion in a plane perpendicular to the engagement direction.

21. A combination comprising:
   the enclosure according to claim 18; and
   the cooperating receptacle comprising:
   receptacle terminal conductors for contacting corresponding ones of said enclosure terminal conductors in the enclosure when engaged with the enclosure; and a base surface along which the enclosure can translate in an engagement direction to engage the enclosure with the receptacle, wherein the receptacle becomes narrower in a direction across the engagement direction with increasing distance into the receptacle along the engagement direction.

22. An absorbent article management system comprising:

a diaper having a receptacle at which sensor elements of the diaper terminate;

a logger unit having logger electronics enclosed in an enclosure according to claim 18 and adapted to cooperate with the receptacle to connect the logger electronics to the sensor elements when the enclosure is engaged with the receptacle; and data processing equipment for processing data acquired from the sensor elements by the logger and for taking action based on the same, wherein the receptacle comprises:

receptacle terminal conductors for contacting corresponding ones of said enclosure terminal conductors in the enclosure when engaged with the enclosure; and a base surface along which the enclosure can translate in an engagement direction to engage the enclosure with the receptacle, wherein the receptacle becomes narrower in a direction across the engagement direction with increasing distance into the receptacle along the engagement direction.

23. An electronics enclosure for engagement with a corresponding receptacle, comprising:

terminal conductors for contacting corresponding conductors in the receptacle when engaged with the receptacle; and a housing having first, second, third, fourth, fifth and sixth surface portions arranged to define the exterior of the housing, wherein the first and second surface portions are respectively front and rear surface portions in an engagement direction of the enclosure with the receptacle, wherein the third and fourth surface portions each connects the first and second surface portions, wherein the fifth and sixth surface portions each connects the first and second surface portions and each connects the third and fourth surface portions and are spaced apart in a direction other than the engagement direction, wherein the third and fourth surface portions each includes a locking depression or projection for engaging a corresponding element of the receptacle to retain the enclosure within the receptacle, and wherein the housing has a depression on an edge joining the rear and lower surface portions and extending at least partly across those surface portions from the edge.

* * * * *